(12) United States Patent
Liu et al.

(10) Patent No.: US 11,627,916 B2
(45) Date of Patent: Apr. 18, 2023

(54) METHOD, STORAGE MEDIUM AND ELECTRICAL DEVICE FOR OBTAINING CYCLE OF PHYSIOLOGICAL SIGNAL

(71) Applicant: Guangzhou Jingcheng Medical Technology Limited, Guangzhou (CN)

(72) Inventors: Xufang Liu, Guangzhou (CN); Song Yang, Guangzhou (CN)

(*) Notice: Subject to any disclaimer, the term of this patent is extended or adjusted under 35 U.S.C. 154(b) by 240 days.

(21) Appl. No.: 15/722,978

(22) Filed: Oct. 2, 2017

(65) Prior Publication Data
US 2018/0020986 A1 Jan. 25, 2018

Related U.S. Application Data

(63) Continuation of application No. 14/362,414, filed on Jun. 3, 2014, now abandoned.

(51) Int. Cl.
| | |
|---|---|
| *A61B 5/00* | (2006.01) |
| *A61B 5/024* | (2006.01) |
| *A61B 5/113* | (2006.01) |
| *A61B 5/352* | (2021.01) |
| *A61B 5/11* | (2006.01) |

(52) U.S. Cl.
CPC ............ *A61B 5/7271* (2013.01); *A61B 5/024* (2013.01); *A61B 5/1135* (2013.01); *A61B 5/352* (2021.01); *A61B 5/7235* (2013.01); *A61B 5/1102* (2013.01)

(58) Field of Classification Search
None
See application file for complete search history.

(56) References Cited

PUBLICATIONS

Bu, Nan, Naohiro Ueno, and Osamu Fukuda. "Monitoring of respiration and heartbeat during sleep using a flexible piezoelectric film sensor and empirical mode decomposition." 2007 29th Annual International Conference of the IEEE Engineering in Medicine and Biology Society. IEEE, 2007. (Year: 2007).*
D'Mello, Yannick, et al. "Real-time cardiac beat detection and heart rate monitoring from combined seismocardiography and gyrocardiography." Sensors 19.16 (2019): 3472. (Year: 2019).*

* cited by examiner

*Primary Examiner* — G Steven Vanni

(57) ABSTRACT

A method for obtaining a cycle of a physiological signal includes: a collection device for collecting a vibration signal of body movements; a processor for obtaining a physiological signal by processing the vibration signal; receiving a physiological signal value and a register value, comparing the physiological signal value with the register value, and reserving one of the physiological signal value and the register value; determining the physiological signal value having a corresponding time duration, reaching a given set time to be an extreme value, wherein the time duration is a time duration of the physiological signal value received is not exceeded; restarting the procedure and determining a next extreme value; obtaining the cycle of the physiological signal by processing the at least one extreme value; and displaying the cycle of the physiological signal in a display device.

6 Claims, 8 Drawing Sheets

METHOD, STORAGE MEDIUM AND ELECTRICAL DEVICE FOR OBTAINING CYCLE OF PHYSIOLOGICAL SIGNAL

CROSS-REFERENCE TO RELATED APPLICATION

The present application is a continuation-in-part of U.S. patent application Ser. No. 14/362,414, filed on Jun. 3, 2014, which is incorporated by reference in its entirety.

BACKGROUND

1. Technical Field

The present disclosure generally relates to technologies for obtaining physiological signals, and more particularly, to a method, a storage medium and an electrical device for obtaining a cycle of a physiological signal.

2. Description of Related Art

Important physiological signals of a human body, such as heartbeat signals and respiration signals, were always obtained by collecting and processing electromyography signals. A signal collecting device needed to contact in tight with human skin for acquiring clear signals which are thereafter amplified and processed. A cycle of the physiological signal obtained in the above way can be obtained as follows: a simple threshold at first is used to set a shaping and obtain a flag bit related to the cycle, then the cycle is obtained by calculating the flag bit of the cycle.

A micro-motion signal of a human body such as a heartbeat signal or a respiration signal (as shown in FIG. 1) sensed by a micro-motion sensor, has a waveform which is totally different from that of a bioelectric signal (as shown in FIG. 2). The waveform includes a different number of wave beams in a skip cycle, a magnitude of the waveform changes linearly according to the cycle, and the cycle cannot be calculated by threshold shaping or simple Fourier transformation. At present, the most common method to calculate the cycle is the real-time heartbeat rate recognition. However, the real-time heartbeat rate recognition method uses the auto-correlation function with a large amount of computation, making it hard to operate the real-time heartbeat rate recognition method in cheap ARMs and thus increasing the cost of obtaining the cycle.

SUMMARY

The main object of the present disclosure is to provide a method for obtaining a cycle of a physiological signal which improves the efficiency of obtaining the cycle of the physiological signal and reduces the cost of obtaining the cycle.

The object of the present disclosure is to achieve by the following technical scheme:

In one aspect, a method for obtaining a cycle of a physiological signal includes:
collecting a vibration signal of body movements using a collection device;
obtaining a physiological signal by processing the vibration signal using a processor;
receiving physiological signal values of the physiological signal and a register value, comparing the physiological signal values with the register value, and reserving one of the physiological signal values and the register value;
determining the physiological signal value having a time duration, reaching a given set time to be an extreme value, wherein the time duration is a time duration of the physiological signal value received is not exceeded;
restarting the procedure and determining a next extreme value;
obtaining a cycle of the physiological signal by processing the at least one extreme value; and
outputting the cycle of the physiological signal to a display device.

Wherein the step of obtaining a cycle of the physiological signal by processing the at least one extreme value includes the following steps:
obtaining a signal cycle both in a positive extreme value and in a negative extreme value in the time duration;
determining whether the two signal cycles respectively obtained in the positive extreme value and in the negative extreme value are close to each other; and
in response to determining that the two signal cycles are close to each other, determining an average of the two signal cycles to be the cycle of the physiological signal.

Wherein the step of receiving physiological signal values of the physiological signal and a register value, comparing the physiological signal values with the register value, and reserving one of the physiological signal values and the register value includes the following steps:
receiving the physiological signal value, starting a counter and incrementing the counter;
comparing the physiological signal value with the register value;
if the physiological signal value is greater than the register value, replacing the register value with the physiological signal value, adding a count value of the counter to an accumulator, clearing the counter to zero, and keeping receiving a next physiological signal value;
if the physiological signal value is not greater than the register value, and keeping receiving a next physiological signal value;
wherein the step of determining the physiological signal value having a corresponding time duration, reaching a given set time to be an extreme value further includes:
when the count value of the counter reaches a value corresponding to the given set time, determining the physiological signal value to be an extreme value; and
outputting the value accumulated in the accumulator, and clearing the counter, a register, and the accumulator, and continuously determining a next extreme value.

Wherein the step of obtaining a cycle of the physiological signal by processing the at least one extreme value includes the following steps:
calculating a time difference between the extreme value and the next extreme value; and
obtaining the cycle of the physiological signal by adding a time required for reaching the value accumulated in the accumulator and the given set time.

Wherein the given set time is longer than a half cycle of an upper limit of a recognition range of the cycle of the physiological signal.

Wherein the step of the processor configured for obtaining the physiological signal by processing the digital signal includes the following steps:
obtaining an analog signal by processing the vibration signal;
converting the analog signal into a digital signal; and
obtaining the physiological signal by processing the digital signal.

In another aspect, An electrical device according to an exemplary embodiment of the present disclosure includes:
a collection device configured for collecting a vibration signal of body movements;
a processor electrically coupled with the collection device;
a memory electrically coupled with the processor and the collection device and configured for computerizing instructions that when executed by the processor, the processor executes a method, including;
obtaining an analog signal by processing the vibration signal;
receiving physiological signal values of the physiological signal and a register value, comparing the physiological signal values with the register value, and reserving one of the physiological signal values and the register value;
determining the physiological signal value having a corresponding time duration, reaching a given set time to be an extreme value, the time duration refers to the time of the physiological signal value received is not exceeded;
restarting the above procedure and determining a next extreme value;
obtaining a cycle of the physiological signal by processing the at least one extreme value; and
a display device electrically coupled with the processor and configured for displaying the cycle of the physiological signal.

Wherein during executing the step of obtaining a cycle of the physiological signal by processing the at least one extreme value, the processor is configured for:
obtaining a signal cycle both in a positive extreme value and in a negative extreme value in the time duration;
determining whether the two signal cycles respectively obtained in the positive extreme value and in the negative extreme value are close to each other; and
in response to determining that the two signal cycles are close to each other, determining an average of the two signal cycles to be the cycle of the physiological signal.

Wherein during executing the step of receiving physiological signal values of the physiological signal and a register value, comparing the physiological signal values with the register value, and reserving one of the physiological signal values and the register value, the processor is configured for:
receiving the physiological signal value, starting a counter and incrementing the counter;
comparing the physiological signal value with the register value;
if the physiological signal value is greater than the register value, replacing the register value with the physiological signal value, adding a count value of the counter to an accumulator, clearing the counter to zero, and keeping receiving a next physiological signal value;
if the physiological signal value is not greater than the register value, and keeping receiving a next physiological signal value;
wherein during executing the step of determining the physiological signal value having a corresponding time duration, reaching a given set time to be an extreme value, the processor is configured for:
when the count value of the counter reaches a value corresponding to the given set time, determining the physiological signal value to be an extreme value;
outputting the value accumulated in the accumulator, and clearing the counter, a register, and the accumulator, and continuously determining a next extreme value; and
wherein during executing the step of obtaining a cycle of the physiological signal by processing the at least one extreme value, the processor is configured for:
calculating a time difference between the extreme value and the next extreme value; and
obtaining the cycle of the physiological signal by adding a time required for reaching the value accumulated in the accumulator and the given set time.

Wherein the given set time is longer than a half cycle of an upper limit of a recognition range of the cycle of the physiological signal.

Wherein the processor further includes:
an analog module configured for obtaining an analog signal by processing the vibration signal;
a converting module configured for converting the analog signal into a digital signal;
a digital module configured for obtaining a physiological signal by processing the vibration signal; wherein
the analog module electrically coupled with the converting module, and the converting module electrically coupled with the digital module.

Wherein the analog module includes an analog amplifying unit, an analog filtering unit and an analog separating unit coupled with each other; the digital module includes a digital amplifying unit, a digital filtering unit and a digital separating unit coupled with each other, the analog separating unit is configured for separating the analog signal into at least one frequency range, the digital separating unit is configured for separate the digital signal into at least one frequency range.

Wherein the collection device is a non-contact collection device.

Wherein the collection device includes a contact-type microphone configured for collecting the vibration signal of body movements.

In a third aspect, non-transitory computer storage medium according to an exemplary embodiment of the present disclosure stores a plurality of commands which are loaded by a processor for executing the commands:
a collection device configured for collecting a vibration signal of body movements;
the processor configured for obtaining a physiological signal by processing the vibration signal;
receiving physiological signal values of the physiological signal and a register value, comparing the physiological signal values with the register value, and reserving one of the physiological signal values and the register value;
determining the physiological signal value having a corresponding time duration, reaching a given set time to be an extreme value, wherein the time duration refers to the time of the physiological signal value received is not exceeded;
restarting the procedure and determining a next extreme value;
obtaining a cycle of the physiological signal by processing the at least one extreme value; and outputting the cycle of the physiological signal to a display device.

Wherein the step of obtaining a cycle of the physiological signal by processing the at least one extreme value further includes the following steps:
obtaining a signal cycle both in a positive extreme value and in a negative extreme value in the time duration;

determining whether the two cycles respectively obtained in the positive extreme value and in the negative extreme value are close to each other; and in response to determining that the two signal cycles are close to each other, determining an average of the two cycles to be the cycle of the physiological signal.

Wherein the step of receiving physiological signal values of the physiological signal and a register value, comparing the physiological signal values with the register value, and reserving one of the physiological signal values and the register value includes the following steps:

receiving the physiological signal value, starting a counter and incrementing the counter;

comparing the physiological signal value with the register value;

if the physiological signal value is greater than the register value, replacing the register value with the physiological signal value, adding a count value of the counter to an accumulator, clearing the counter to zero, and keeping receiving a next physiological signal value;

if the physiological signal value is not greater than the register value, and keeping receiving a next physiological signal value;

wherein the step of determining the physiological signal value having a time duration, reaching a given set time to be an extreme value includes the following steps:

when the count value of the counter reaches a value corresponding to the given set time, determining the physiological signal value to be an extreme value; and outputting the value accumulated in the accumulator, and clearing the counter, a register, and the accumulator, and continuously determining a next extreme value.

Wherein the step of obtaining a cycle of the physiological signal by processing the at least one extreme value includes the following steps:

calculating a time difference between the extreme value and the next extreme value; and obtaining the cycle of the physiological signal by adding a time required for reaching the value accumulated in the accumulator and the given set time.

Wherein the given set time is longer than a half cycle of an upper limit of a recognition range of the cycle of the physiological signal.

wherein the step of obtaining the physiological signal by processing the digital signal includes:

obtaining an analog signal by processing the vibration signal;

converting the analog signal into a digital signal; and obtaining the physiological signal by processing the digital signal.

The present disclosure provides the advantages as below.

In the present disclosure, the collection device is configured for collecting the vibration signals caused by body movements such as heartbeat, breathing and turning over. The processor is configured for obtaining a physiological signal by processing the vibration signal from the collection device. The processor also provides a series of corrections and transformations of the vibration signal, such as amplification, filtering and separation to easily process the physiological signal obtained. In this way, not only it can effectively reduce the data process power of the hardware, but also it can effectively reduce the computation of the hardware and greatly reduce the production cost of the electrical device for obtaining the cycle of the physiological signal. Obtaining an extreme value by comparing the physiological signal value with the register value, and obtaining a cycle of the physiological signal by processing the at least one extreme value. The processor is configured for executing the computer programs to obtain all or part of the method for obtaining a cycle of a physiological signal which is mentioned above. In this way, the cycle of the physiological signal can be obtained by the extreme value recognition algorithm, which is simple, fast, of high efficiency, and of high reliability. Furthermore, the calculation of the cycle does not use the floating-point multiplication, the cycle is obtained only through a few comparators and counters. In this way, the requirements about the amplification of the physiological signal, the filtering of the physiological signal, and the analogy-to-digital conversion are relatively low and the data process is relatively simple, thus, the hardware cost and the hardware computation can be greatly reduced and the calculation speed of the hardware can be also improved. Furthermore, the sharp reduction of the storage space allows to use cheap, low-power processors rather than big-storage, high-speed, high-performance, and high-power processors. In addition, the cycle of the physiological signal is output to the display device and effectively displayed in the display device. Thus, It is not only convenient to view, but also can interact with the graphical interface shown on the display device by operating the graphical interface.

BRIEF DESCRIPTION OF THE DRAWINGS

Many aspects of the embodiments can be better understood with reference to the following drawings. The components in the drawings are not necessarily dawns to scale, the emphasis instead being placed upon clearly illustrating the principles of the embodiments. Moreover, in the drawings, like reference numerals designate corresponding parts throughout the several views.

Figure 1:
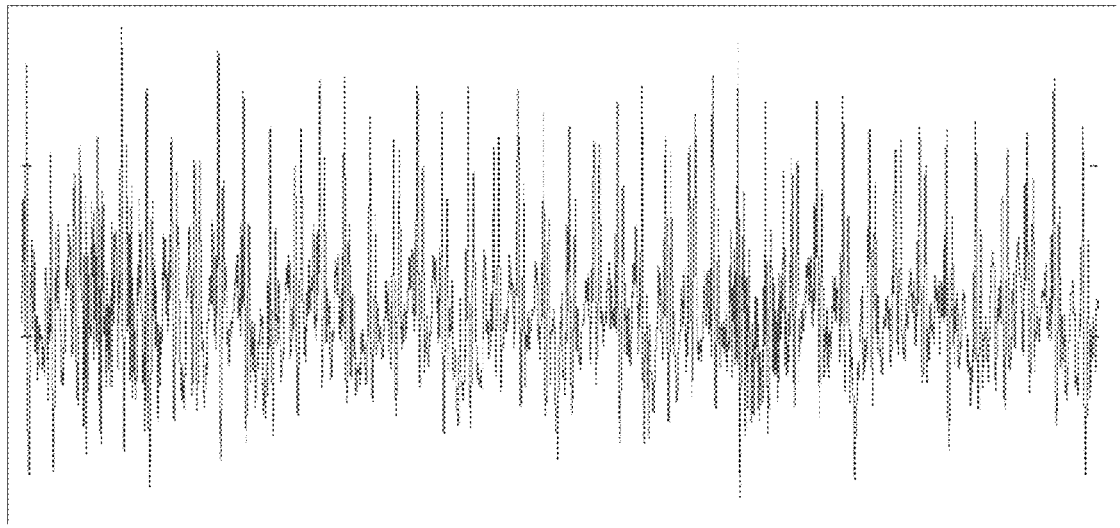
FIG. 1 is a schematic view of a waveform of a signal obtained by a piezoelectric sensor in a related art.
Figure 2:
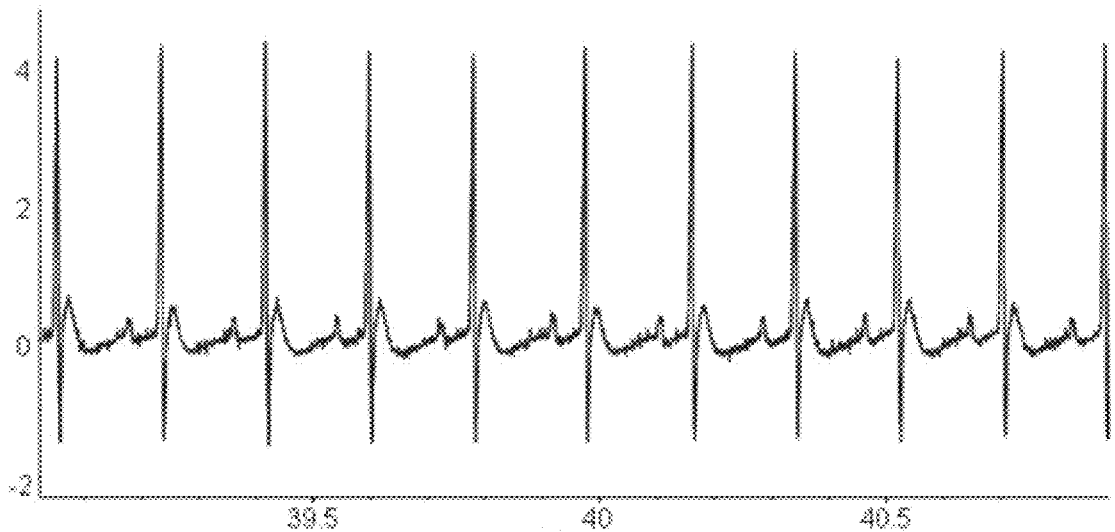
FIG. 2 is a schematic view of a waveform of a bioelectric signal in the related art.

The element labels according to the exemplary embodiment of the present disclosure shown as below:

electrical device 100, collection device 101, processor 102, memory 103, display device 104, analog module 105, analog amplifying unit 1050, analog filtering unit 1051, analog separating unit 1052, converting module 106, digital module 107, digital amplifying unit 1070, digital filtering unit 1071, digital separating unit 1072, counter 108, comparator 109, register 110.

DETAILED DESCRIPTION

The disclosure is illustrated by way of example and not by way of limitation in the figures of the accompanying drawings, in which like reference numerals indicate similar elements.

In the description of the present disclosure, it is to be understood that the terms such as "center", "transverse", "up", "down", "left", "right", "vertical", "horizontal", "top", "bottom", "inside" and "outside" are indicated as a location or a position based on the location or the position shown in the drawings. It is only is to facilitate and simplify the description of the present disclosure, rather than to indicate or imply that the device or element which is referred to have a specific orientation, constructed and operated by a particular orientation, therefore it cannot be interpreted as a limitation of the present disclosure. In addition, the terms "first", "second" are used to describe the purpose only, and cannot be construed as indicating or implying the relative importance or the number of technical features indicated by the implied designation. Thus, the features of "first" and "second" can be indicated or implied to include one or more of these features. In the description of the present disclosure, unless otherwise stated, the term "a plurality of" means two or more. In addition, the term "include" and its any deformation, is intent to overwrite the inclusion that does not exclude it.

In the description of the present disclosure, unless otherwise specified, it is to be noted that the terms "installation", "connect to" and "connect with" should be understood in a broad sense. For example, it may be a fixed connection, or a detachable connection, or an integral connection. It may be a mechanically connection or an electrically connection. It also may be directly connected, or indirectly connected by an intermediate medium, which may be internally connected within two components. For a skilled person in the related art, it is understood that the concrete implication of the above-mentioned terms in the present disclosure according to the specific conditions.

The terms used here are simply to describe the concrete embodiments rather than intent to limit the exemplary embodiments. Unless otherwise implied of the context explicitly, the singular form terms used herein "a" and "one" are intent to include the plural. It is also to be understood that the terms used herein "include" and/or "comprise" are the provisions stated the features, integers, steps, operations, institutions and/or components, rather than exclude the existence or add one or more other features, integers, steps, operations, institutions, components and/or their combination.

In the figures, the configuration with a similar structure is shown in a same label.

The present disclosure is further illustrated by way of a preferred exemplary embodiment and the drawings.

Figure 3:
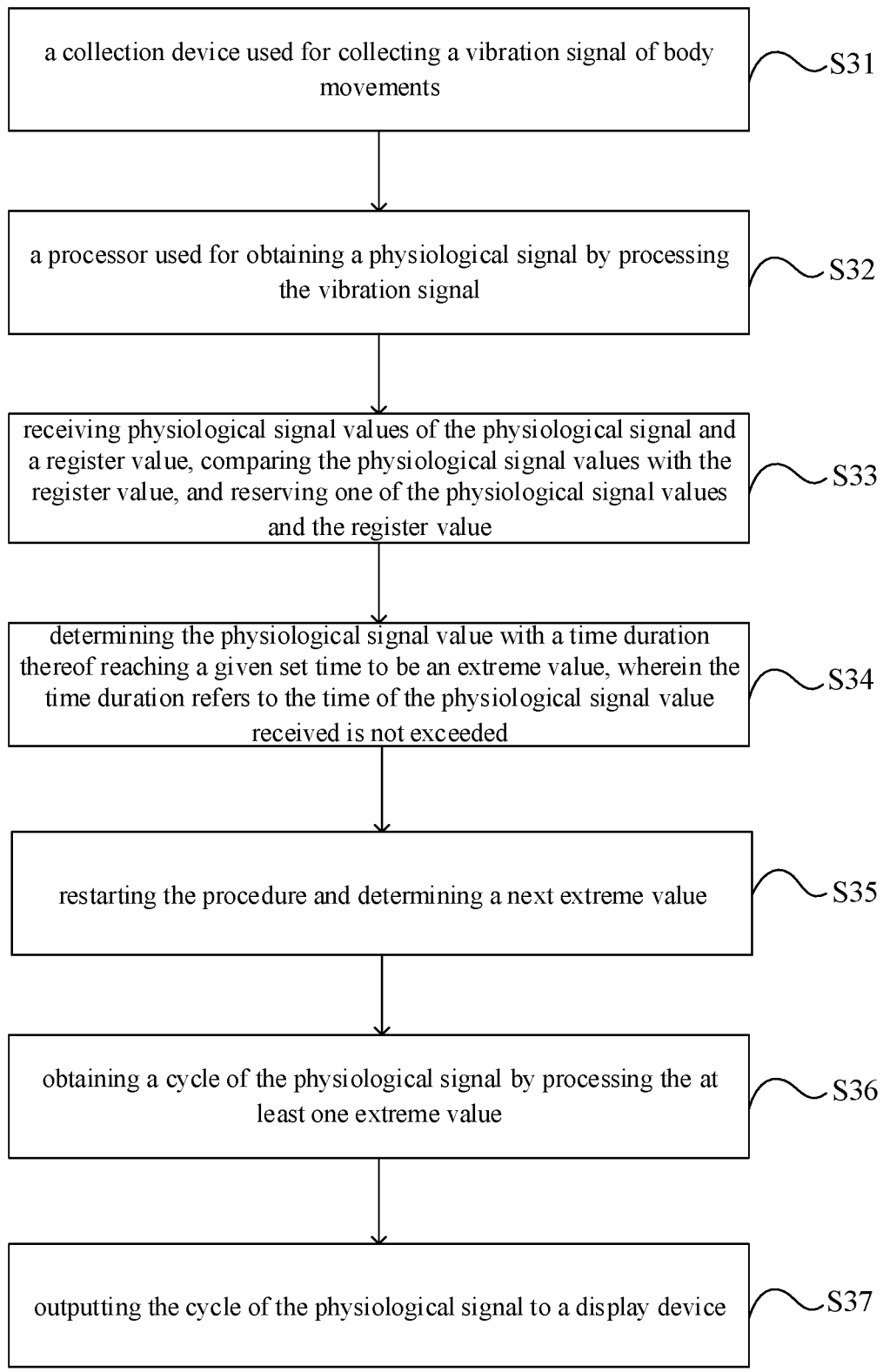
FIG. 3 is a flow chart of a method for obtaining a cycle of a physiological signal in accordance with an exemplary embodiment of the present disclosure.
Figure 9:
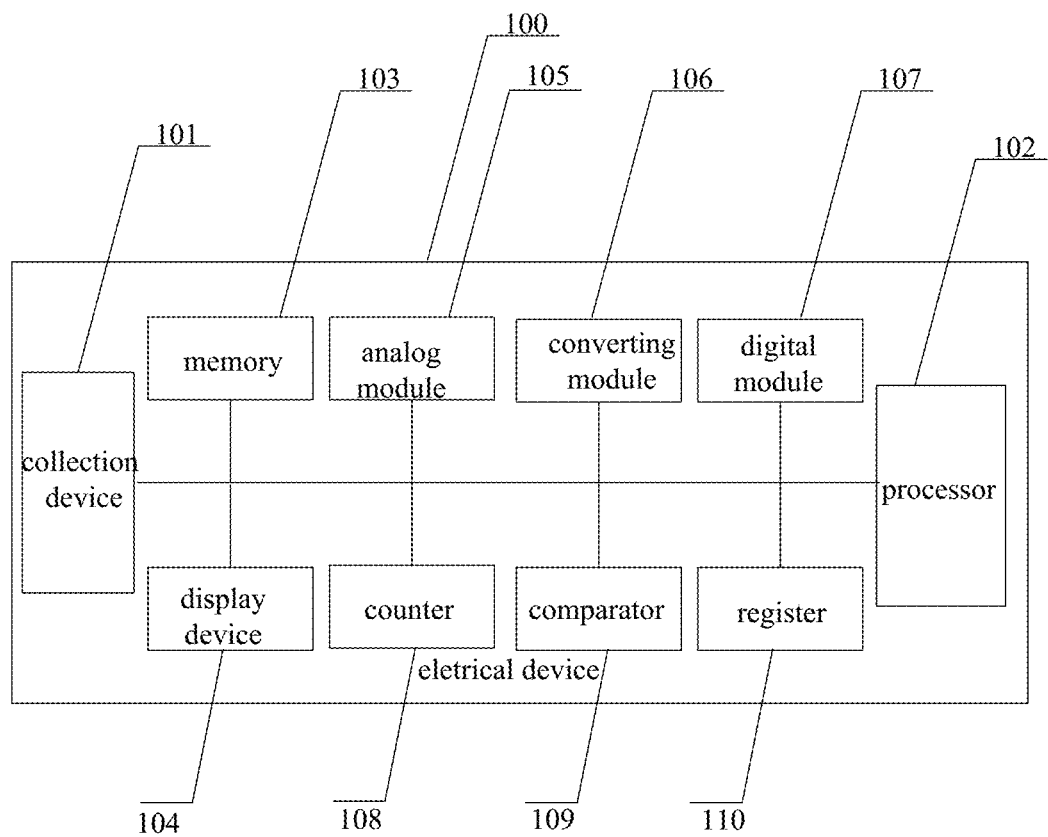
FIG. 9 is another schematic view of the electrical device of FIG. 8.

Referring to FIG. 3 and FIG. 9, a method for obtaining a cycle of a physiological signal includes the following steps:

S31: collecting a vibration signal of body movements using a collection device.

Furthermore, the collection device may be a piezoelectric sensor or a contact-type microphone. A micro-motion sensor such as the piezoelectric sensor can be used for obtaining a micro-vibration signal of a human body when the human body is in a quiet state. The contact-type microphone does not need to direct contact with a human body, rather than contact with the human body via the transitional structure such as clothing, mattresses, sheets, bedding. When the human body is in a quiet state, the vibration signal of body movements such as heartbeat, breathing can be captured by the contact-type microphone.

S32: obtaining an analog signal by processing the vibration signal using a processor.

It is understood, the processor is configured for obtaining a physiological signal by processing a series of corrections and transformations of the vibration signal, such as amplification, filtering and separation in order to more conveniently indentify and process the physiological signal obtained. In this way, not only it can effectively reduce the data process power of the hardware, but also it can effectively reduce the computation of the hardware. The physiological signal can be a respiration signal or a heartbeat signal processed by the processor, the physiological signal value can be a specific value such as a voltage.

S33: receiving physiological signal values of the physiological signal and a register value, comparing the physiological signal values with the register value, and reserving one of the physiological signal values and the register value.

The above step specifically includes: receiving the physiological signal value, starting a counter 108 and adding an unit value to the counter 108, and comparing the physiological signal value with the register value; if the physiological signal value is greater than the register value in the register 110, replacing the register value with the physiological signal value and storing in the register 110, adding a count value of the counter 108 to an accumulator, clearing the counter 108 to zero, and keeping receiving a next physiological signal value; if the physiological signal value is no greater than the register value, keeping receiving a next physiological signal value.

The above step specifically also includes: receiving the physiological signal value, starting a counter 108 and adding an unit value to the counter 108, and comparing the physiological signal value with the register value; if the physiological signal value is less than the register value in the register 110, replacing the register value with the physiological signal value and storing in the register 110, adding a count value of the counter 108 to an accumulator, clearing the counter 108 to zero, and keeping receiving a next physiological signal value; if the physiological signal value is no less than the register value, keeping receiving a next physiological signal value.

S34: determining the physiological signal value having a corresponding time duration, reaching a given set time to be an extreme value, wherein the time duration is a time duration of the physiological signal value received is not exceeded.

The above step specifically includes: when the count value of the counter 108 reaches a value corresponding to the given set time, determining the physiological signal value to be an extreme value, outputting the value accumulated in the accumulator, and clearing the counter 108, the register 110, and the accumulator, and continuously determining a next extreme value. The register value can be equal to zero or the reserved physiological signal value.

S35: restarting the above procedure and determining a next extreme value.

It is understood that the above steps S31 to S34 can be repeated to obtain a plurality of extreme values, thereby the calculation of the cycle of the physiological signal is more accurate by selecting and processing the plurality of extreme values.

S36: obtaining a cycle of the physiological signal by processing the at least one extreme value.

The cycle of the physiological signal can be obtained by the extreme value recognition algorithm shown on the steps above, which is simple, fast, of high efficiency, and of high reliability. Furthermore, the calculation of the cycle does not use the floating-point multiplication, the cycle is obtained only through a few comparators and counters. In this way, the requirements about the amplification of the physiological signal, the filtering of the physiological signal, and the analogy-to-digital conversion are relatively low and the data process is relatively simple, thus, the hardware cost and the hardware computation can be greatly reduced and the calculation speed of the hardware can be also improved. Furthermore, the sharp reduction of the storage space allows to use cheap, low-power processors rather than big-storage, high-speed, high-performance, and high-power processors.

S37: outputting the cycle of the physiological signal to a display device.

Furthermore, the cycle of the physiological signal is output to the display device and effectively displayed in the display device. Thus, It is not only convenient to view, but also can interact with the graphical interface shown on the display device by operating the graphical interface.

According to the above method mentioned, the collection device is configured for collecting the vibration signals caused by body movements such as heartbeat, breathing and turning over. The processor is configured for obtaining a physiological signal by processing the vibration signal from the collection device. The processor also provides a series of corrections and transformations of the vibration signal, such as amplification, filtering and separation to easily process the physiological signal obtained. In this way, not only it can effectively reduce the data process power of the hardware, but also it can effectively reduce the computation of the hardware and greatly reduce the production cost of the electrical device for obtaining the cycle of the physiological signal. Obtaining an extreme value by comparing the physiological signal value with the register value, and obtaining the cycle of the physiological signal by processing the at least one extreme value. The processor is configured for executing the computer programs to obtain all or part of the method for obtaining a cycle of a physiological signal which is mentioned above. In this way, the cycle of the physiological signal can be obtained by the extreme value recognition algorithm, which is simple, fast, of high efficiency, and of high reliability. Furthermore, the calculation of the cycle does not use the floating-point multiplication, the cycle is obtained only through a few comparators and counters. In this way, the requirements about the amplification of the physiological signal, the filtering of the physiological signal, and the analogy-to-digital conversion are relatively low and the data process is relatively simple, thus, the hardware cost and the hardware computation can be greatly reduced and the calculation speed of the hardware can be also improved. Furthermore, the sharp reduction of the storage space allows to use cheap, low-power processors rather than big-storage, high-speed, high-performance, and high-power processors. In addition, the cycle of the physiological signal is output to the display device and effectively displayed in the display device. Thus, It is not only convenient to view, but also can interact with the graphical interface shown on the display device by operating the graphical interface.

The cycle of the physiological signal can be obtained by an extreme value recognition algorithm. The extreme value can be a positive extreme value or a negative extreme value, that is, the current extreme value and the next extreme value can respectively be a positive extreme value or a negative extreme value. The positive extreme value recognition algorithm can be: timing a duration when one received physiological signal value is kept greatest, and determining the received physiological signal value to be a positive extreme value in one cycle when the timer reaches the given set time. The time difference (time length) between the positive extreme value (the extreme value) and a next positive extreme value (the next extreme value) can be calculated. The negative extreme value recognition algorithm can be: timing a duration when one received physiological signal is kept smallest, and determining the received physiological signal value to be a negative extreme value in one cycle when the timer reaches the given set time. Furthermore, the time difference between the negative extreme value (the extreme value) and a next negative extreme value (the next extreme value) can be calculated. The cycle of the physiological signal obtained by the positive extreme value recognition algorithm and the cycle of the physiological signal obtained by the negative extreme value recognition algorithm are respectively obtained according to the given set time and the time difference between the two positive extreme values or the time difference between the two negative extreme values. The given set time can be set according to the specific physiological signal, for example, in the embodiment the given set time can be longer than a half of the cycle of the physiological signal.

Figure 4:
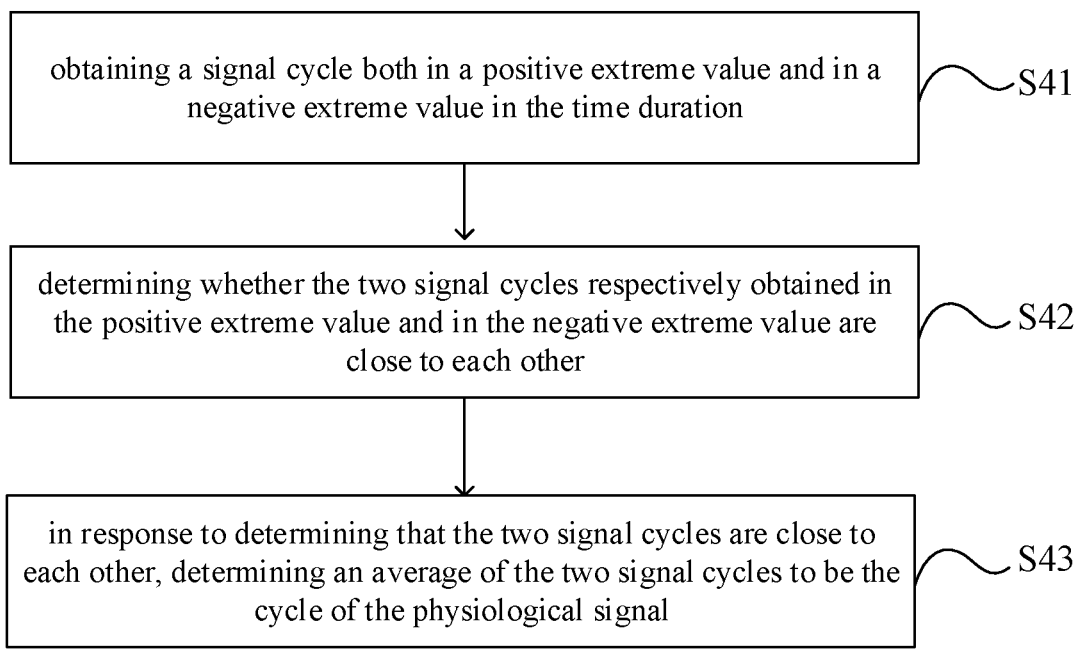
FIG. 4 is a flow chart of a step of obtaining a cycle of the physiological signal by processing the at least one extreme value.

Referring to FIG. 4, a flow chart of a step of obtaining a cycle of the physiological signal by processing the at least one extreme value is shown. The step includes the following sub-steps:

S41: obtaining a signal cycle both in a positive extreme value and in a negative extreme value in the time duration;

S42: determining whether the two signal cycles respectively obtained in the positive extreme value and in the negative extreme value are close to each other; and S43: in response to determining that the two signal cycles are close to each other, determining an average of the two signal cycles to be the cycle of the physiological signal.

In a given set time duration, for example, at least one cycle of the physiological signal obtained in the positive extreme value and at least one cycle of the physiological signal obtained in the negative extreme value are obtained. The cycles obtained in the two ways are compared with each other to judge whether the two cycles are close to each other. If the two cycles are close to each other, averaging the two cycles and determining the average of the two cycles to be the more accurate cycle of the physiological signal, otherwise ending the procedure. Whether the two cycles are close to each other or not can be judged according to the specific type of the physiological signal, for example, the time difference between two close cycles of a respiration signal is approximately 1-10 milliseconds and the time difference between two close cycles of a heartbeat signal is approximately 1-40 milliseconds.

In the above method for obtaining the cycle of the physiological signal, the cycle of the physiological signal can be obtained by the extreme value recognition algorithm, which is simple, fast, of high efficiency, and of high reliability; furthermore, the requirements about the amplification of the physiological signal, the filtering of the physiological signal, and the analogy-to-digital conversion are relatively low and the data process is relatively simple, thus, the hardware cost can be greatly reduced.

Figure 5:
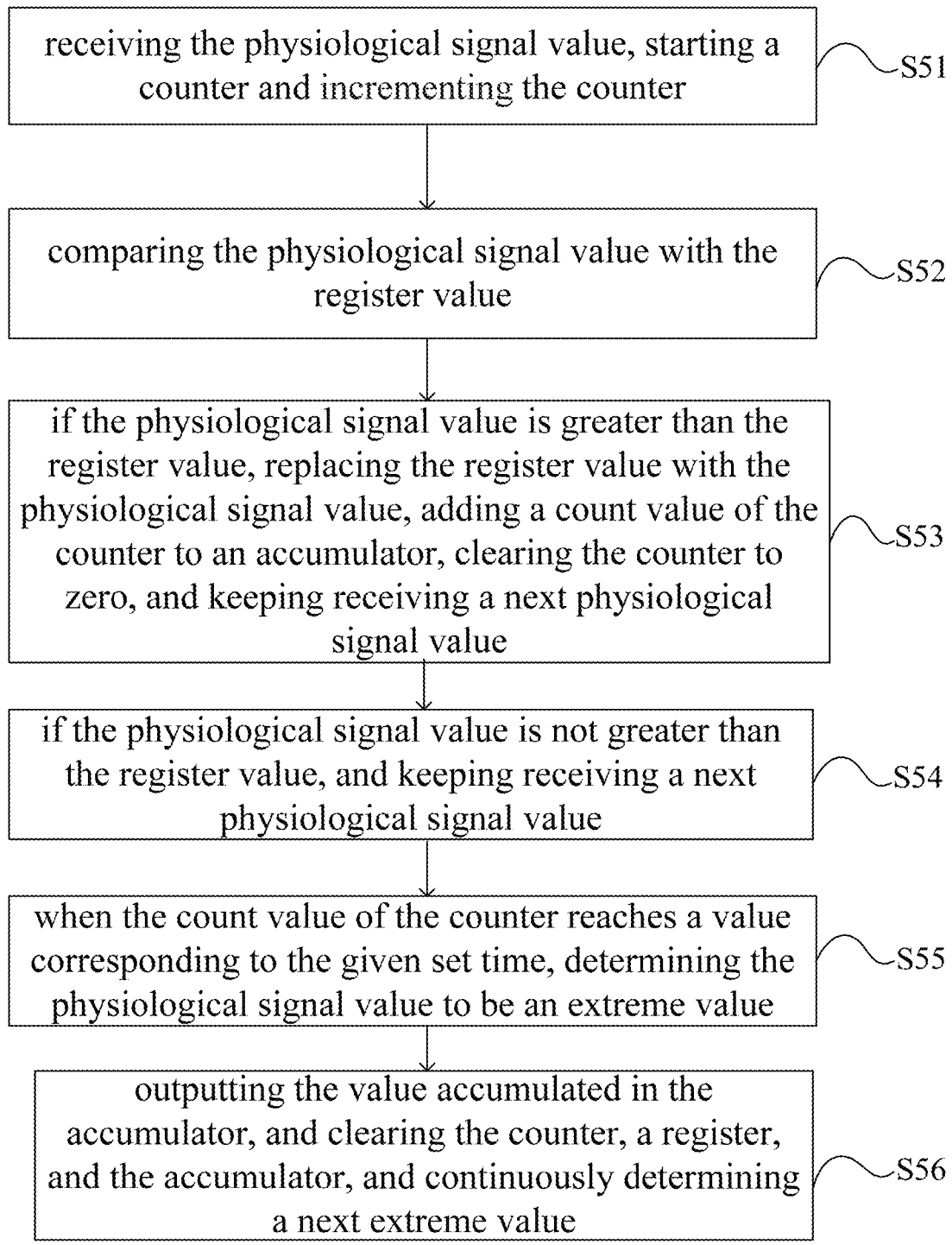
FIG. 5 is a flow chart of a step of receiving physiological signal values of the physiological signal and a register value, comparing the physiological signal values with the register value, and reserving one of the physiological signal values and the register value.

Referring to FIG. 5 and FIG. 9, a flow char of a step of receiving physiological signal values of the physiological signal and a register value, comparing the physiological signal values with the register value, and reserving one of the physiological signal values and the register value is shown. The step includes the following sub-steps:

S51: receiving the physiological signal value, starting a counter and incrementing the counter;

S52: comparing the physiological signal value with the register value;

S53: if the physiological signal value is greater than the register value, replacing the register value with the physiological signal value, adding a count value of the counter to an accumulator, clearing the counter to zero, and keeping receiving a next physiological signal value;

S54: if the physiological signal value is not greater than the register value, and keeping receiving a next physiological signal value.

The step of determining the physiological signal value having a corresponding time duration, reaching a given set time to be an extreme value includes the following sub-steps:

S55: when the count value of the counter reaches a value corresponding to the given set time, determining the physiological signal value to be an extreme value;

S56: outputting the value accumulated in the accumulator, and clearing the counter, a register, and the accumulator, and continuously determining a next extreme value.

The above step specifically includes: receiving the physiological signal value, starting a counter 108 and adding an unit value to the counter 108, and comparing the physiological signal value with the register value; if the physiological signal value is greater than the register value in the register 110, replacing the register value with the physiological signal value and storing in the register 110, adding a count value of the counter 108 to an accumulator, clearing the counter 108 to zero, and keeping receiving a next physiological signal value; if the physiological signal value is no greater than the register value, keeping receiving a next physiological signal value; when the count value of the counter reaches a value corresponding to the given set time, determining the physiological signal value to be an extreme value, outputting the value accumulated in the accumulator, and clearing the counter 108, the register 110, and the accumulator, and continuously determining a next extreme value. The register value can be equal to zero or the reserved physiological signal value.

The method for obtaining the above physiological signal can further be described as follows based on the following example in which the cycle of the physiological signal is obtained in the positive extreme value.

At first, receiving a voltage of a heartbeat signal outputted from the piezoelectric sensor, starting the counter 108 and adding 1 to the counter 108, comparing the count value of the counter 108 with the register value in the register 110; if the count value is greater than the register value, replacing the register value with the count value, adding the count value of the counter 108 to the accumulator, and clearing the counter 108 to zero; if the count value is less than the register value; keeping receiving the next voltage of the heartbeat signal.

Outputting the value accumulated in the accumulator, clearing the counter 108, the register 110, and the accumulator, and starting a new cycle when the count value of the counter 108 reaches a corresponding value. Each heartbeat signal received in the new cycle is compared with the register value 0 in the register 110. The formula for calculating the cycle of the above heartbeat signal is expressed as:

Cycle(s)=(the value accumulated in the accumulator/a receiving speed of the physiological signal)+the given set time.

Since the constant of the time duration (that is, the given set time) when the physiological signal is kept being greatest needs to be previously set, thus, an upper limit of the recognition cycle can be the reciprocal of the given set time.

For example, if the frequency of the heartbeat signal ranges from 0.7 Hz to 1.6 Hz, then the given set time of the positive extreme value is 0.55 seconds (the given set time of the negative extreme value is 0.6 seconds). If a received heartbeat signal is kept being greatest in the register 110 for 0.55 seconds, then the counter starts to count. Adding 1 to the counter 108 when a new heartbeat signal is inputted into the comparator. If the voltage of the new heartbeat signal is greater than the previous register value, storing the voltage of the new heartbeat signal in the register 110 and replacing the previous register value with the voltage, adding the count value of the counter 108 to the accumulator, and clearing the counter 108 to zero. If the voltage of the new heartbeat signal is not greater than the previous register value stored in the register 110, adding 1 to the counter 108, continuing the cycle of comparing the voltage of the heartbeat signal, outputting a value B accumulated in the accumulator until the count value of the counter 108 is equal to the number of the voltages (for example, 300) of the heartbeat signals received in 0.55 seconds, and adding 0.55 seconds and the time required for reaching the value B accumulated in the accumulator to acquire the cycle of the heartbeat signal.

Supposed that the number of the received heartbeat signals counted by the counter 108 in 0.55 seconds when one heartbeat signal is kept being greatest is 275, and the speed of receiving the heartbeat signal is 500 per second, then the cycle of the heartbeat signal=(B/500)+0.55.

According to the above method, the cycle of the physiological signal is respectively obtained in the positive extreme value and in the negative extreme value in a time duration, thereafter the more accurate cycle of the physiological signal can be obtained according to the cycle of the physiological signal obtained in the positive extreme value and the cycle of the physiological signal obtained in the negative extreme value.

The step of obtaining the negative extreme value specifically includes: receiving the physiological signal value, starting a counter 108 and adding an unit value to the counter 108, and comparing the physiological signal value with the register value; if the physiological signal value is less than the register value, replacing the register value with the physiological signal value, adding a count value of the counter 108 to an accumulator, and clearing the counter 108 to zero; if the physiological signal value is no greater than the register value, keeping receiving a next voltage of the physiological signal; when the count value of the counter 108 reaches a value corresponding to the given set time, determining the physiological signal value to be an extreme value, outputting the value accumulated in the accumulator, and clearing the counter 108, a register 110, and the accumulator, and continuously determining a next extreme value. The register value can be equal to zero or the reserved physiological signal value.

Figure 6:
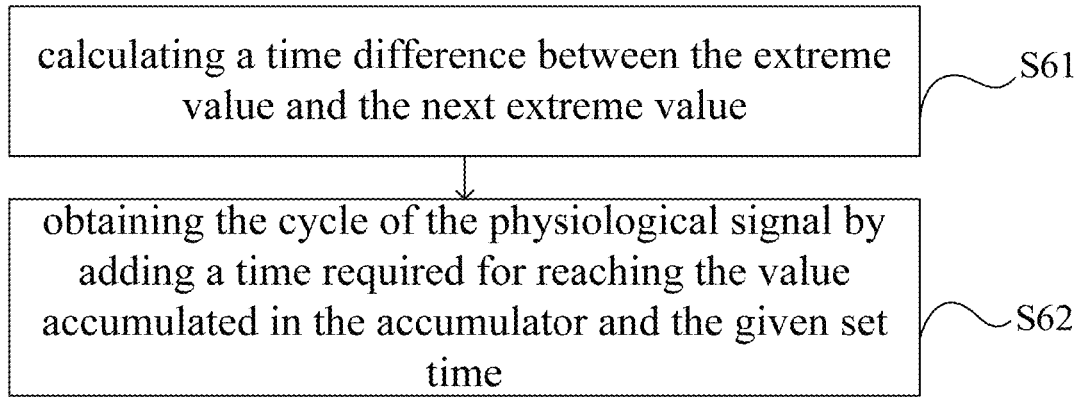
FIG. 6 is a flow chart of a step of obtaining a cycle of the physiological signal by processing the at least one extreme value.

Referring to FIG. 6, a flow chart of a step of obtaining a cycle of the physiological signal by processing the at least one extreme value is shown. The step includes the following sub-steps:

S61: calculating a time difference between the extreme value and the next extreme value; and S62: obtaining the cycle of the physiological signal by adding a time required for reaching the value accumulated in the accumulator and the given set time.

Determining a feature point by finding the locus that maintains in the positive extreme value or in the negative extreme value more than a certain time thereof in a signal cycle, obtaining a cycle of the heartbeat signal by calculating a time difference between the two feature points, and then calculating a frequency of the heartbeat signal. Thus, it can effectively reduce the computation of the hardware and improve the calculation speed. Furthermore, the sharp reduction of the storage space allows to use cheap, low-power processors rather than big-storage, high-speed, high-performance, and high-power processors.

The given set time is longer than a half cycle of an upper limit of a recognition range of the cycle of the physiological signal.

Figure 7:
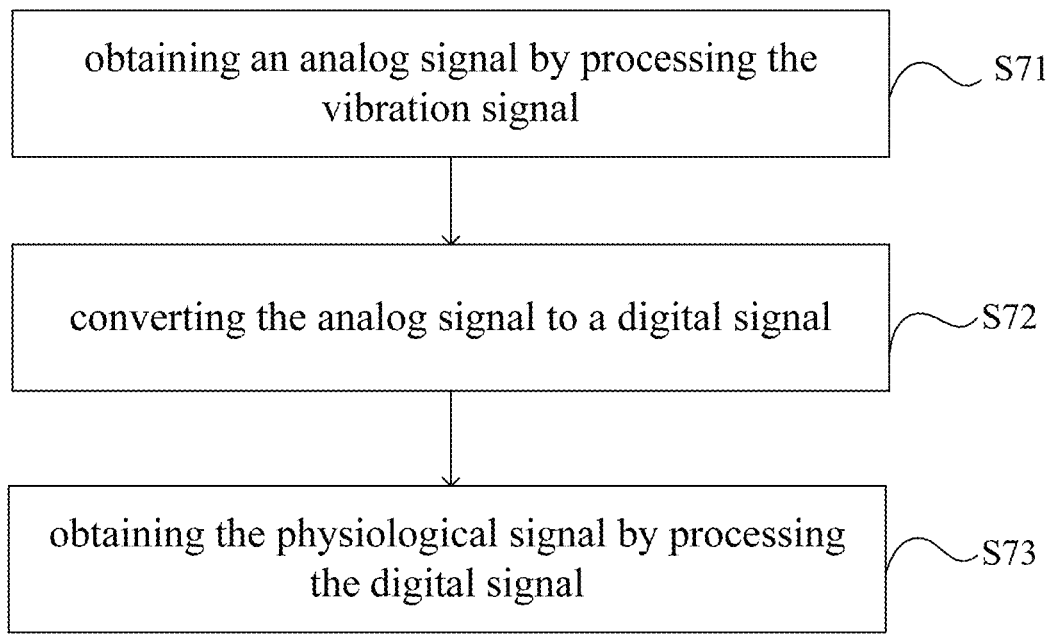
FIG. 7 is a flow chart of a step of obtaining the physiological signal by processing the digital signal.

Referring to FIG. 7, the flow chart of the step of the processor configured for obtaining the physiological signal by processing the digital signal is shown. The step includes the following sub-steps:

S71: obtaining an analog signal by processing the vibration signal;

S72: converting the analog signal into a digital signal;

S73: obtaining the physiological signal by processing the digital signal.

The step of converting the analog signal into a digital signal also includes: amplifying, filtering and separating the analog signal/digital signals into the signals with different frequency ranges, which can effectively enhance the analog signal/digital signal and further improve the accuracy of the cycle of the physiological signal. The processor can be selected from the MSP430F6723 chip of TI company or the ADUC chip of ADI company to complete the analog-to-digital conversion, the digital filtering and the cycle calculation.

Figure 8:
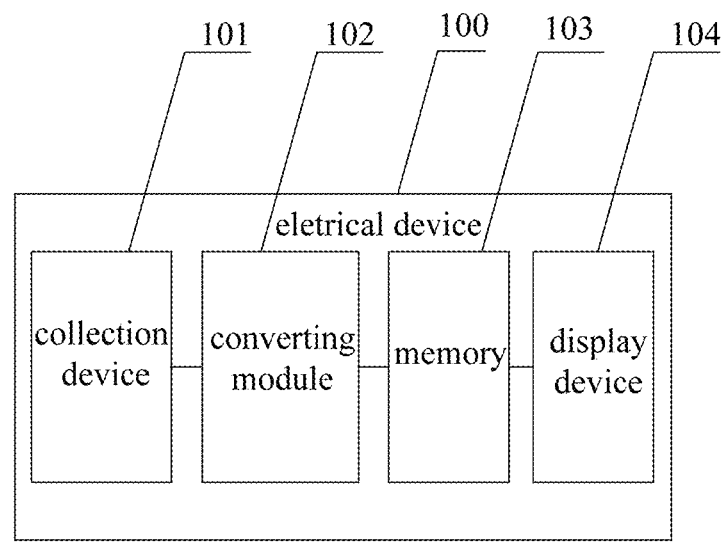
FIG. 8 is a schematic view of an electrical device for obtaining a cycle of a physiological signal in accordance with an exemplary embodiment of the present disclosure.
Figure 10:
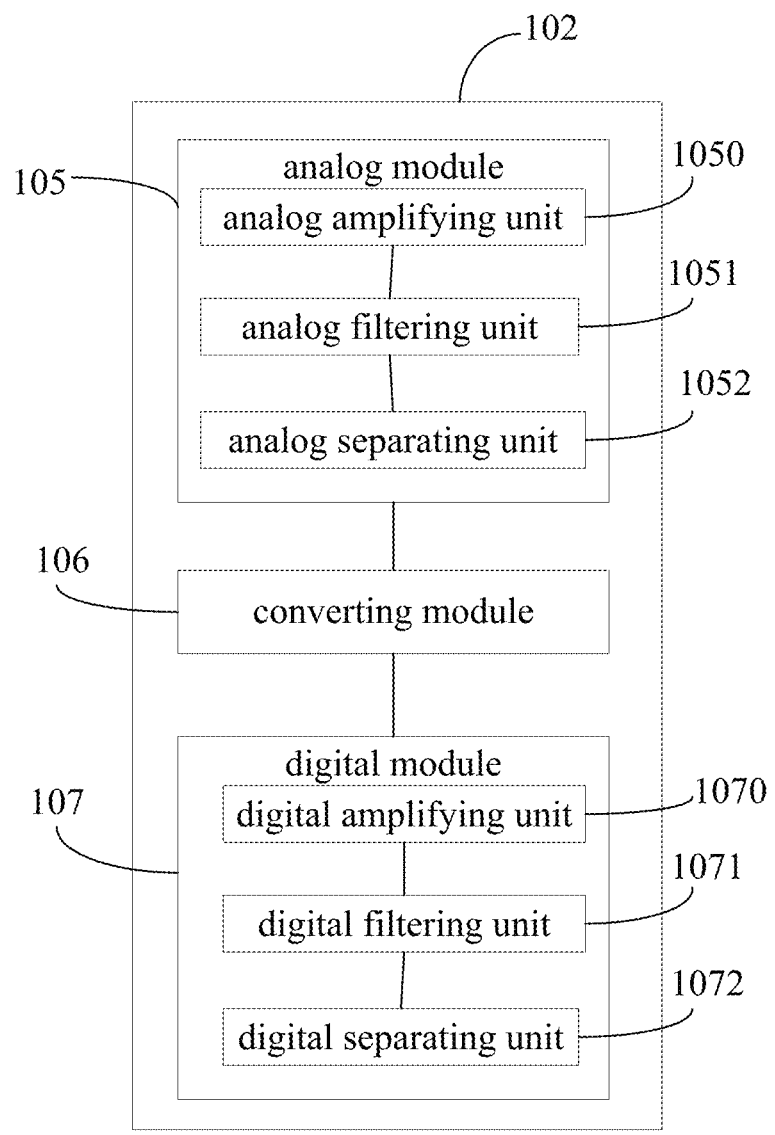
FIG. 10 is a schematic view of a processor of the electrical device of FIG. 8.

Referring to FIGS. 8-10, an electrical device 100 configured for obtaining a cycle of a physiological signal is shown. The electrical device 100 includes a collection device 101, a processor 102, a memory 103 and a display device 104.

The collection device 101 is configured for collecting a vibration signal of body movements;

The processor 102 is electrically coupled with the collection device 101.

The processor 101 is configured for obtaining a physiological signal by processing the vibration signal;

receiving physiological signal values of the physiological signal and a register value, comparing the physiological signal values with the register value, and reserving one of the physiological signal values and the register value;

determining the physiological signal value having a corresponding time duration, reaching a given set time to be an extreme value, wherein the time duration refers to the time of the physiological signal value received is not exceeded;

restarting the above procedure and determining a next extreme value; and obtaining a cycle of the physiological signal by processing the at least one extreme value.

The collection device 101 is configured for collecting the vibration signals caused by body movements such as heartbeat, breathing and turning over. The processor 102 is configured for obtaining a physiological signal by processing the vibration signal from the collection device 101. The processor 102 also provides a series of corrections and transformations of the vibration signal, such as amplification, filtering and separation to easily process the physiological signal obtained. In this way, not only it can effectively reduce the data process power of the hardware, but also it can effectively reduce the computation of the hardware and greatly reduce the production cost of the electrical device 100 for obtaining the cycle of the physiological signal. Obtaining an extreme value by comparing the physiological signal value with the register value, and obtaining the cycle of the physiological signal by processing the at least one extreme value. The processor 102 is configured for executing the computer programs to obtain all or part of the method for obtaining a cycle of a physiological signal which is mentioned above. In this way, the cycle of the physiological signal can be obtained by the extreme value recognition algorithm, which is simple, fast, of high efficiency, and of high reliability. Furthermore, the calculation of the cycle does not use the floating-point multiplication, the cycle is obtained only through a few comparators and counters. In this way, the requirements about the amplification of the physiological signal, the filtering of the physiological signal, and the analogy-to-digital conversion are relatively low and the data process is relatively simple, thus, the hardware cost and the hardware computation can be greatly reduced and the calculation speed of the hardware can be also improved. Furthermore, the sharp reduction of the storage space allows to use cheap, low-power processors rather than big-storage, high-speed, high-performance, and high-power processors.

The memory 103 is electrically coupled with the processor 102 and the collection device 101 and configured for storing data and computer programs which is run in the processor 102;

The display device 104 is electrically coupled with the processor 102 and configured for displaying the cycle of the physiological signal.

The cycle of the physiological signal is output to the display device 104 and effectively displayed in the display device 104. Thus, It is not only convenient to view, but also can interact with the graphical interface shown on the display device 104 by operating the graphical interface.

The cycle of the physiological signal can be obtained by the extreme value recognition algorithm, and the actual current consumption ranges at 1 mA to 2 mA level. Comparatively speaking, the similar-function implementation of the same-type products mostly requires the signal with a long time (for example 20 seconds) to perform Fourier transformation. For example, if the sampling rate is 500 BPS, it is needed to process 10K level floating point numbers to execute Fourier transformation at the same time. In this way, its calculation is more than 1000 times that of the present method, and the power consumption is also considerable, thereby it is difficult to support such calculations with batteries. Therefore, in addition to our method, most of the other equipments in the industry require an external DC power to support the calculation of the cycle.

Furthermore, during executing the step of obtaining the cycle of the physiological signal by processing the at least one extreme value, the processor 102 is configured for:

obtaining a signal cycle both in a positive extreme value and in a negative extreme value in the time duration;

determining whether the two signal cycles respectively obtained in the positive extreme value and in the negative extreme value are close to each other; and in response to determining that the two signal cycles are close to each other, determining an average of the two signal cycles to be the cycle of the physiological signal.

In the given set time duration, for example, at least one cycle of the physiological signal obtained in the positive extreme value and at least one cycle of the physiological signal obtained in the negative extreme value are obtained. The cycles obtained in the two ways are compared with each other to judge whether the two cycles are close to each other. If the two cycles are close to each other, averaging the two cycles and determining the average of the two cycles to be the more accurate cycle of the physiological signal, otherwise ending the procedure. Whether the two cycles are close to each other or not can be judged according to the specific type of the physiological signal. The cycle of the physiological signal can be obtained by the extreme value recognition algorithm, which is simple, fast, of high efficiency, and of high reliability; furthermore, the requirements about the amplification of the physiological signal, the filtering of the physiological signal, and the analogy-to-digital conversion are relatively low and the data process is relatively simple, thus, the hardware cost can be greatly reduced.

During executing the step of receiving physiological signal values of the physiological signal and a register value, comparing the physiological signal values with the register value, and reserving one of the physiological signal values and the register value, the processor 102 is configured for:

receiving the physiological signal value, starting a counter and incrementing the counter;

comparing the physiological signal value with the register value;

if the physiological signal value is greater than the register value, replacing the register value with the physiological signal value, adding a count value of the counter to an accumulator, clearing the counter to zero, and keeping receiving a next physiological signal value;

if the physiological signal value is not greater than the register value, and keeping receiving a next physiological signal value;

wherein during executing the step of determining the physiological signal value having a corresponding time duration, reaching a given set time to be an extreme value, the processor is configured for:

when the count value of the counter reaches a value corresponding to the given set time, determining the physiological signal value to be an extreme value;

outputting the value accumulated in the accumulator, and clearing the counter, a register, and the accumulator, and continuously determining a next extreme value; and wherein during executing the step of obtaining a cycle of the physiological signal by processing the at least one extreme value, the processor is configured for:

calculating a time difference between the extreme value and the next extreme value; and obtaining the cycle of the physiological signal by adding a time required for reaching the value accumulated in the accumulator and the given set time.

Determining a feature point by finding the locus that maintains in the positive extreme value or in the negative extreme value more than a certain time thereof in a signal cycle, obtaining a cycle of the heartbeat signal by calculating a time difference between the two feature points, and then calculating a frequency of the heartbeat signal. Thus, it can effectively reduce the computation of the hardware and improve the calculation speed. Furthermore, the sharp reduction of the storage space allows to use cheap, low-power processors rather than big-storage, high-speed, high-performance, and high-power processors.

The given set time is longer than a half cycle of an upper limit of a recognition range of the cycle of the physiological signal.

Furthermore, the processor 102 further includes an analog module 105, a converting module 106 and a digital module 107.

The analog module 105 and the digital module 107 are integrated on the processor 102 and respectively configured for processing the vibration signal and the digital signal passed through the processor 102.

The converting module 106 is optional as an analog-to-digital converter, namely an A/D converter, or an ADC for short and usually refers to an electrical component that transforms an analog signal into a digital signal. The general A/D converter converts an input voltage signal to an output digital signal.

The analog module 105 is configured for obtaining an analog signal by processing the vibration signal.

The converting module 106 is configured for converting the analog signal into a digital signal.

The digital module 107 is configured for obtaining a physiological signal by processing the vibration signal; and The analog module 105 is electrically coupled with the converting module 106, and the converting module 106 is electrically coupled with the digital module 107.

The collection device 101 is configured for collecting a vibration signal caused by body movements such as heartbeat, breathing and turning over. The analog module 105 is configured for obtaining an analog signal by processing the vibration signal and transmitting the analog signal to the converting module 106. The converting module 106 is configured for obtaining a digital signal by processing the analog signal and converting the digital signal to the digital module 107. The digital module 107 is configured for obtaining a physiological signal by processing the digital signal. In addition, the analog module 105 is configured for amplifying, filtering and separating the analog signal into at least one frequency range, and the digital module 107 is configured for amplifying, filtering and separating the analog signal into at least one frequency range, thereby the converting module 106 and the digital module 107 may easily process the signal obtained. In this way, not only it can effectively improve the calculation speed of the processor 102, but also it can effectively enhance the analog signal and further greatly improve the accuracy of obtaining the cycle of the physiological signal. At the same time, the requirements about the amplification of the physiological signal, the filtering of the physiological signal, and the analogy-to-digital conversion are relatively low and the data process is relatively simple, thus, the hardware cost and the hardware computation can be greatly reduced.

Furthermore, the analog module 105 includes an analog amplifying unit 1050, an analog filtering unit 1051 and an analog separating unit 1052 coupled with each other. The digital module 107 includes a digital amplifying unit 1070, a digital filtering unit 1071 and a digital separating unit 1072 coupled with each other. The analog separating unit 1052 is configured for separating the analog signal into at least one frequency range, and the digital separating unit 1072 is configured for separate the digital signal into at least one frequency range. For example, the analog signal may be divided into a low frequency analog signal, an intermediate frequency analog signal and a high frequency analog signal, the digital signal may also be divided into a low frequency digital signal, an intermediate frequency digital signal and a high frequency digital signal. In this way, the processor 102 can be more convenient to classify and rapid process the analog signal and the digital signal, thereby improve the operation efficiency of the processor 102. The analog module 105 is configured for obtaining an analog signal by processing the vibration signal to amplify and filter the analog signal. The converting module 106 is configured for obtaining a digital signal by analogy-to-digital conversion, and the digital module 107 is configured for processing the digital signal. In addition, the present method of the present disclosure finds a loci with the characteristics in the input digital signal and measure the time length of two adjacent locus, thereby obtain the cycle of the physiological signal.

In addition, the processor 102 further includes an executing unit corresponding to the number of the frequency range. Each executing unit is configured for processing a signal of a frequency range by setting the executing unit corresponding to the number of frequencies, thereby the operation efficiency and the calculation speed of the processor 102 can be effectively improved, and the calculation accuracy of obtaining the cycle of the physiological signal can be greatly improved.

Furthermore, the processor 102 includes a processing chip which the analog module 105, the converting module 106 and the digital module 107 are integrated thereon. In this way, the volume of the electrical device 100 is greatly reduced and more portable to conveniently use. Of course, the analog module 105, the converting module 106 and the digital module 107 can be physically located on at least two independent processing chips, which is helpful for heat dissipation between the modules. Thus, it can greatly improve the operation efficiency of the processor 102 and further greatly improve the accuracy of obtaining the cycle of the physiological signal. The processing chip can be selected from the MSP430F6723 chip of TI company or the ADUC chip of ADI company to complete the analog-to-digital conversion, the digital filtering and the cycle calculation.

Meanwhile, the collection device 101 includes a contact-type microphone configured for collecting the vibration signal of body movements, with the frequency of the vibration signal ranges from 0.1 Hz to 200 Hz. The contact-type microphone does not need to direct contact with a human body, rather than contact with the human body via the transitional structure such as clothing, mattresses, sheets, bedding. When the human body is in a quiet state, the vibration signal of body movements such as heartbeat, breathing can be captured by the contact-type microphone. The physiological information such as heartbeats, respirations, and tossing and turnings can be obtained by analyzing the vibration signal.

By obtaining mechanical vibration signals of the human body, at present, the general heartbeat signal sensed relies on the collection of biological signals, such as ECG signals. A signal collecting electrodes needed to direct contact with human skin, rather than contacted with the human body by an insulation fabric such as clothing, mattresses and bedding, for acquiring standard ECG signals. In this way, after amplified and filtered, a series of highly consistent voltage waves that appear in chronological order is obtained. The present disclosure is configured for collecting the vibration signals caused by the body movements such as heartbeat, breathing and turning over. The vibration signal can be different due to mattresses, sheets, clothes, and sleeping positions. However, the conventional method can neither effectively process the mechanical vibration signals nor effectively obtain a cycle of the physiological signal, thereby resulting in the measurement of the cycle of the physiological signal inaccuracy.

The electrical device 100 includes the processor 102, the memory 103, the display device 104 and a control circuit (not shown). For a skilled person in the related art, it is understood that the structure of the electrical device 100 shown in the figures cannot be interpreted as a limitation of the electrical device 100. The electrical device 100 may include components more or less than that shown in the figures of the present disclosure, or combinations of some components, or different components arranged thereon. It is needed to state that the electrical device 100 includes smart phones, tablet computers and so on.

Furthermore, the processor 102 is provided as the control center of the electrical device 100 and connects with all parts of the electrical device 100 by using various interfaces and wires. The processor 102 is configured for executing the plurality of functional applications and processing data of the electrical device 100 to monitor the whole electrical device 100 by running/executing the programs or recalling the data stored within the memory 103.

In accordance with the following commands below, the processor 102 loads one or more than one application process corresponding to an executable file into the memory 103, and run the programs stored in the memory 103 to realize various functions.

The memory 103 is configured for storing programs and data. The program stored in the memory 103 includes a plurality of executable program codes to form a plurality of function modules. The processor 102 is configured for executing the plurality of functional applications and processing data via running the programs stored in memory 103.

The display device 104 is configured for displaying the information input from a user to the electrical device 100, or displaying the information provided to the user and various graphical user interface of the electrical device 100. The graphical user interfaces can be composed of graphics, text, icons, videos, and any combination of them.

The control circuit is electrically connected to the display device 104 and configured for controlling the state of the display device 104 in the scheduling of the processor 102.

The electrical device 100 may further include radio frequency (RF) circuits to send and receive the RF signals, such as building communication links with a plurality of servers and receiving the packets sent from the server.

In some other embodiments of the present disclosure, the electrical device 100 may include a power supply configured for providing power for all parts of the electrical device 100. The power supply may be logically connected with the processor 102 by a power management system so as to manage charge, discharge and power consumption via the power management system.

Although it's not shown in FIGS. 8-9, the electrical device 100 may also include a camera, a blue-tooth module and so on, which is not repeated here.

A non-transitory computer storage medium in accordance with an exemplary embodiment of the present disclosure is provided. The computer storage medium stores a plurality of commands which is loaded by a processor for executing:

a vibration signal;

the processor configured for obtaining the physiological signal by processing the digital signal of body movements collected by the collection device;

receiving physiological signal values of the physiological signal and a register value, comparing the physiological signal values with the register value, and reserving one of the physiological signal values and the register value;

determining the physiological signal value having a corresponding time duration, reaching a given set time to be an extreme value, wherein the time duration refers to the time of the physiological signal value received is not exceeded;

restarting the procedure and determining a next extreme value; and obtaining a cycle of the physiological signal by processing the at least one extreme value; and outputting the cycle of the physiological signal to a display device.

Furthermore, the step of obtaining a cycle of the physiological signal by processing the at least one extreme value further includes:

obtaining a signal cycle both in a positive extreme value and in a negative extreme value in the time duration;

determining whether the two signal cycles respectively obtained in the positive extreme value and in the negative extreme value are close to each other; and in response to determining that the two signal cycles are close to each other, determining an average of the two signal cycles to be the cycle of the physiological signal.

Furthermore, the step of receiving physiological signal values of the physiological signal and a register value, comparing the physiological signal values with the register value, and reserving one of the physiological signal values and the register value includes the following steps:

receiving the physiological signal value, starting a counter and incrementing the counter;

comparing the physiological signal value with the register value;

if the physiological signal value is greater than the register value, replacing the register value with the physiological signal value, adding a count value of the counter to an accumulator, clearing the counter to zero, and keeping receiving a next physiological signal value;

if the physiological signal value is not greater than the register value, and keeping receiving a next physiological signal value;

wherein the step of determining the physiological signal value having a corresponding time duration, reaching a given set time to be an extreme value includes the following steps:

when the count value of the counter reaches a value corresponding to the given set time, determining the physiological signal value to be an extreme value; and outputting the value accumulated in the accumulator, and clearing the counter, a register, and the accumulator, and continuously determining a next extreme value.

Furthermore, the step of obtaining a cycle of the physiological signal by processing the at least one extreme value includes the following steps:

calculating a time difference between the extreme value and the next extreme value; and obtaining the cycle of the physiological signal by adding a time required for reaching the value accumulated in the accumulator and the given set time.

Furthermore, the given set time is longer than a half cycle of an upper limit of a recognition range of the cycle of the physiological signal.

Furthermore, the step of obtaining the physiological signal by processing the digital signal of body movements collected by the collection device includes the following steps:

obtaining an analog signal by processing the vibration signal;

converting the analog signal into a digital signal; and obtaining the physiological signal by processing the digital signal.

For a skilled person in the related art, it is understood that all or part of the steps of the method of the present embodiments can be done by commands, or can be done by controlling the associated hardware through the commands. The command may be stored in a computer readable medium, for example stored in the memory 103 of the electrical device 100, and loaded to execute by the at least one processor of the electrical device 100. In addition, the readable medium may include a ROM (Read Only Memory), a RAM (Random Access Memory), a disk or a CD.

Figure 11:
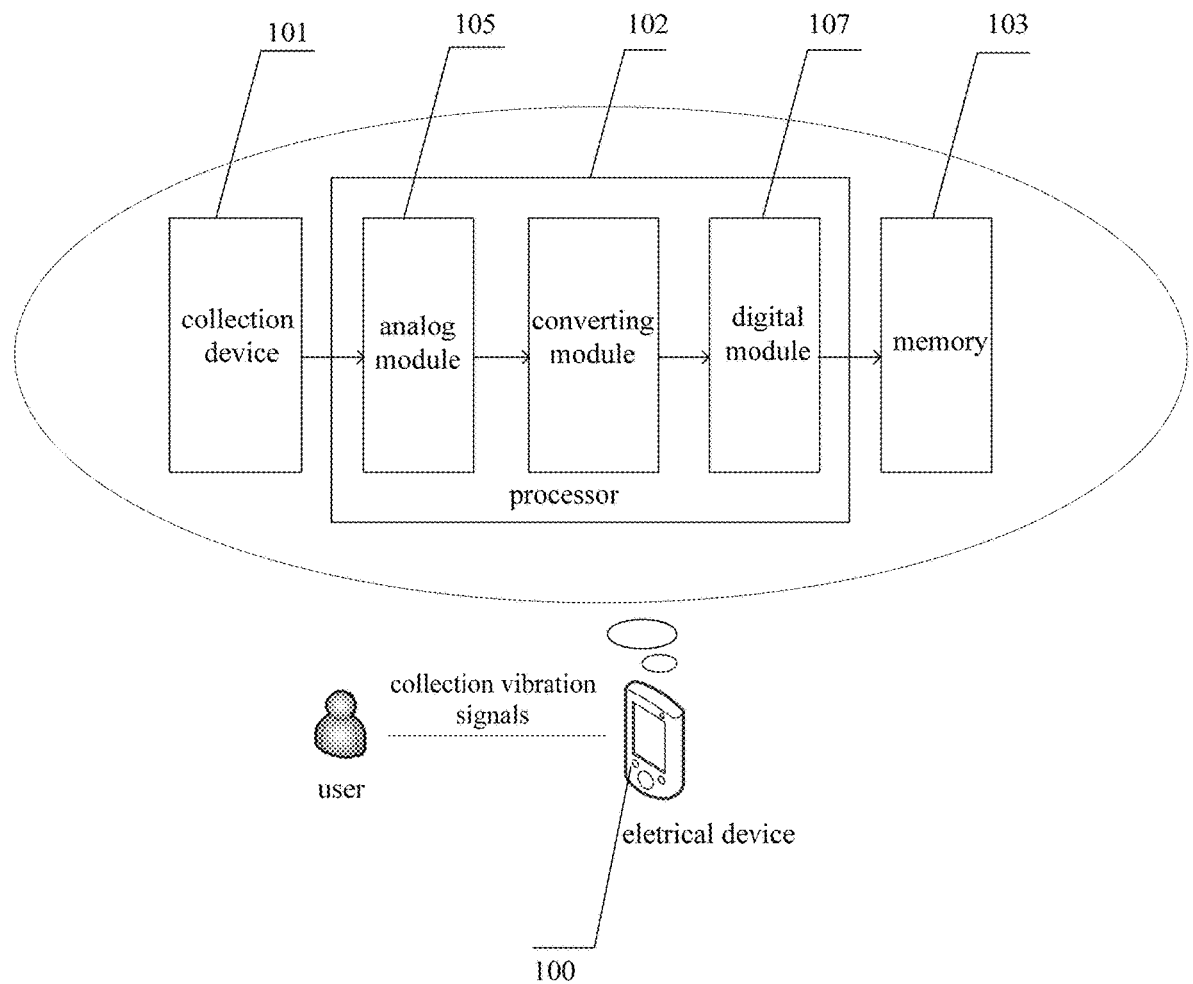
FIG. 11 is a schematic view of a method for obtaining a cycle of a physiological signal in accordance with an exemplary embodiment of the present disclosure, shown in a using state.

FIG. 11 is shown in a using state of the method for obtaining a cycle of the physiological signal. The electrical device 100 is mainly configured for obtaining a cycle of a physiological signal by processing the vibration signal collected. In accordance with the preset commands, the processor 102 of the electrical device 100 loads one or more than one application process corresponding to an executable file into the memory 103, and run the programs stored in the memory 103 to realize various functions.

Even though information and the advantages of the present embodiments have been set forth in the foregoing description, together with details of the mechanisms and functions of the present embodiments, the disclosure is illustrative only; and that changes may be made in detail, especially in matters of shape, size, and arrangement of parts within the principles of the present embodiments to the full extend indicated by the broad general meaning of the terms in which the appended claims are expressed.

What is claimed is:

1. A method for obtaining a cycle time of a physiological signal obtained from piezoelectric devices, comprising:
   S1, receiving physiological signal values of the physiological signal, from the piezoelectric devices, comparing the received physiological signal values with a temporarily stored value, and reserving one of the physiological signal values or the temporarily stored value;
   S2, determining the temporarily stored value as a first extreme value if the temporarily stored value has not been replaced by the received physiological signal values when a reserving time reaches a preset time period;
   S3, restarting the steps of S1 and S2 to obtain a next extreme value; and
   S4, obtaining a time period from the first extreme value to the next extreme value, and determining the time period as the cycle time of the physiological signal;
   wherein the physiological signal comprises a respiratory signal and a heartbeat signal; the first extreme value and the next extreme value are defined as a maximum value or a minimum value in the preset time period; and the preset time period is shorter than the cycle time of the physiological signal.

2. The method of claim 1, further comprising:
   determining an average value of a first time period from obtaining the first extreme value to the next extreme value and the second time period from obtaining the first extreme value to the next extreme value as the cycle time of the physiological signal.

3. A piezoelectric device for obtaining a cycle a cycle time of a physiological signal comprising:
   a contact-type microphone configured for obtaining the physiological signal;

a processor electrically coupled with the contact-type microphone; and a memory electrically coupled with the processor and the contact-type microphone and configured to store computerized instructions and, when executed by a processor, to cause the processor to perform a method, the method comprising:

S1, receiving physiological signal values of the physiological signal, from the piezoelectric devices, comparing the received physiological signal values with a temporarily stored value, and reserving one of the physiological signal values or the temporarily stored value;

S2, determining the temporarily stored value as a first extreme value if the temporarily stored value has not been replaced by the received physiological signal values when a reserving time reaches a preset time period;

S3, restarting the steps of S1 and S2 to obtain a next extreme value; and

S4, obtaining a time period from the first extreme value to the next extreme value, and determining the time period as the cycle time of the physiological signal;

wherein the physiological signal comprises a respiratory signal and a heartbeat signal; the first extreme value and the next extreme value are defined as a maximum value or a minimum value in the preset time period; and the preset time period is shorter than the cycle time of the physiological signal.

4. The piezoelectric device of claim 3, wherein the processor is configured for: determining an average value of a first time period from obtaining the first extreme value to the next extreme value and the second time period from obtaining the first extreme value to the next extreme value as the cycle time of the physiological signal.

5. A non-transitory computer storage medium configured to store computerized instructions and, when executed by a processor, to cause the processor to perform a method, the method comprising:

S1, receiving physiological signal values of the physiological signal, from the piezoelectric devices, comparing the received physiological signal values with a temporarily stored value, and reserving one of the physiological signal values or the temporarily stored value;

S2, determining the temporarily stored value as a first extreme value if the temporarily stored value has not been replaced by the received physiological signal values when a reserving time reaches a preset time period;

S3, restarting the steps of S1 and S2 to obtain a next extreme value; and

S4, obtaining a time period from the first extreme value to the next extreme value, and determining the time period as the cycle time of the physiological signal;

wherein the physiological signal comprises a respiratory signal and a heartbeat signal; the first extreme value and the next extreme value are defined as a maximum value or a minimum value in the preset time period; and the preset time period is shorter than the cycle time of the physiological signal.

6. The non-transitory computer storage medium of claim 5, wherein the processor is further caused to perform a method of determining an average value of a first time period from obtaining the first extreme value to the next extreme value and the second time period from obtaining the first extreme value to the next extreme value as the cycle time of the physiological signal.

* * * * *